United States Patent [19]
Nakamura et al.

[11] Patent Number: 5,306,087
[45] Date of Patent: Apr. 26, 1994

[54] APPARATUS FOR THERMOGRAVIMETRY

[75] Inventors: Nobutaka Nakamura; Haruo Takeda; Yoshiharu Sugano, all of Tokyo, Japan

[73] Assignee: Seiko Instruments Inc., Tokyo, Japan

[21] Appl. No.: 934,391

[22] Filed: Aug. 25, 1992

[30] Foreign Application Priority Data

Aug. 26, 1991 [JP] Japan .................. 3-213965

[51] Int. Cl.⁵ .................. G01G 23/18; G01N 25/00
[52] U.S. Cl. .................. 374/14; 177/245
[58] Field of Search .................. 374/14; 177/245

[56] References Cited
U.S. PATENT DOCUMENTS 4,606,649  8/1986  Mikail .................. 374/14 X
4,846,292  7/1989  Narukawa .................. 177/245 X

OTHER PUBLICATIONS

"Automated Thermoanalytical Techniques": An Automated Thermobalance W. S. Bradley et al. Analytical Chemistry vol. 43, No. 2, Feb. 1971 pp. 223-227.

Primary Examiner—Daniel M. Yasich
Attorney, Agent, or Firm—Spensley Horn Jubas and Lubitz

[57] ABSTRACT

Apparatus for conducting thermogravimetric analysis continuously when sample weights are measured automatically in the case of measurement of a plurality of samples. A plurality of empty sample containers are transferred individually in succession from a tray to a thermobalance, where each container is weighed and a representation of the weight of each empty container is stored in a first memory. Then, a sample is loaded into each container in the tray and the loaded sample containers are transferred individually in succession from the tray to the thermobalance where each loaded container is weighed and a representation of the weight of each container is stored in a second memory. The weight of each sample is then determined based on the difference between the representations stored in the first and second memories.

6 Claims, 1 Drawing Sheet

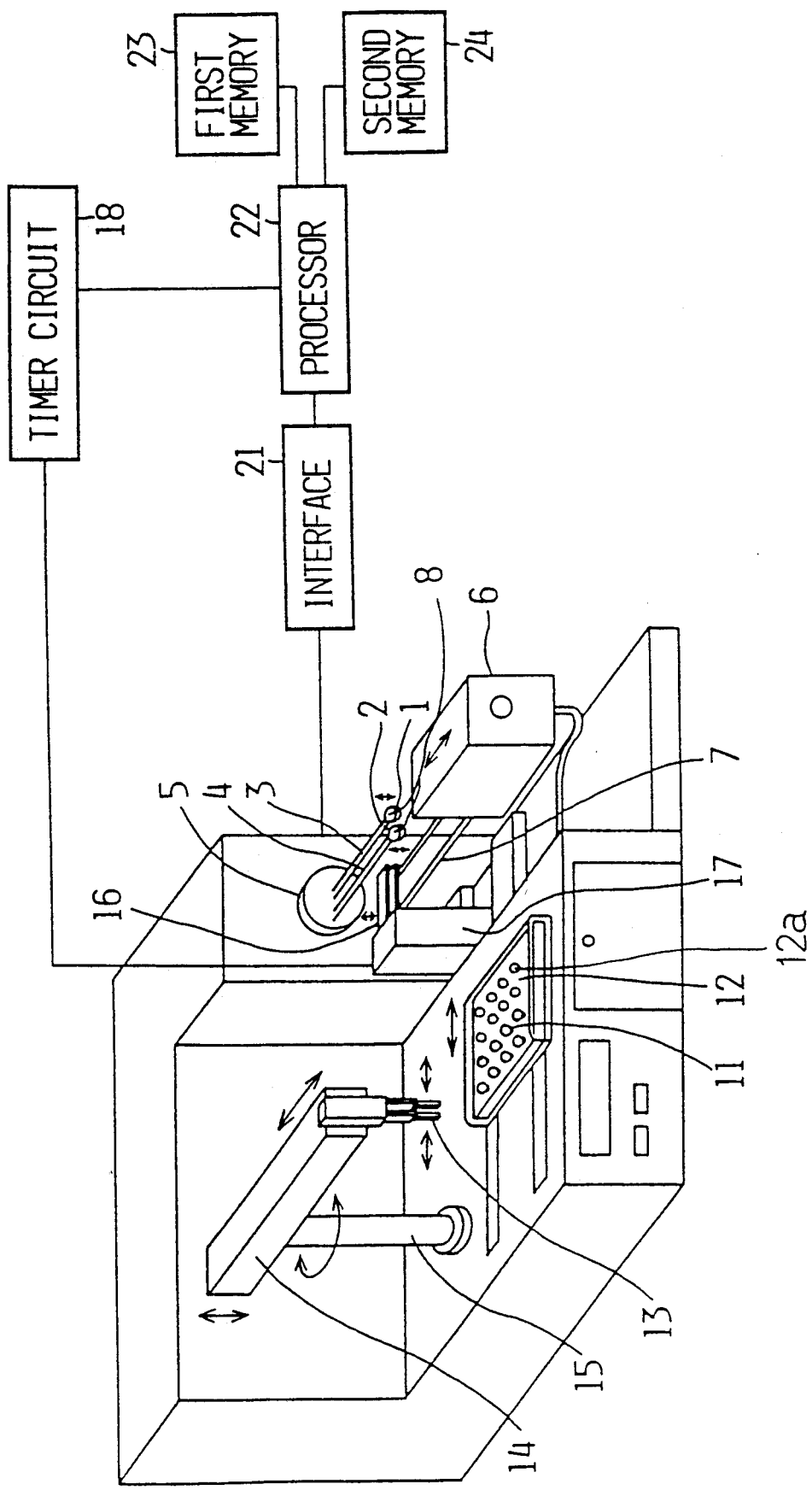

APPARATUS FOR THERMOGRAVIMETRY

BACKGROUND OF THE INVENTION

The present invention relates to an apparatus for thermogravimetry which automatically measures the weight changes of each of a plurality of samples, which weight changes depend on sample temperature when the operation of sample conveyance and the operation of thermogravimetry are alternately and automatically performed.

Thermogravimetric analysis in thermal analysis is a relatively old technique which began with the Honda type of thermobalance.

Even though the usefulness of thermogravimetric analysis is now widely known, thermogravimetry apparatus which can automatically measure a plurality of samples is relatively unknown. In conventional apparatus for thermogravimetry, as disclosed in Japanese Patent Application Laid Open No. 720331983, the following methods are used: the initial weight of a sample before thermal analysis is preliminarily measured by a worker with a chemical balance; or the weight output obtained when an empty sample container is set on an apparatus is used as a reference, and the variation of weight output obtained when a sample is loaded in the sample container is used as the weighed value.

When thermogravimetric analysis for a plurality of samples is automatically conducted, for example, samples are put in platinum sample containers in order to minimize staining of the apparatus which is caused when the samples are heated. Therefore, it is rather difficult to measure only the initial weight of samples. For example, in the case where about 50 samples are measured with a chemical balance, measurement with respect to one sample must be conducted once before and once after the sample is loaded in a sample container, and it is necessary to then determine the weight difference. Depending on the configuration of the samples, this can take about 2 hours in total. Since the samples must be manually loaded in the sample containers, it is impossible to measure a plurality of samples continuously and automatically.

SUMMARY OF THE INVENTION

An object of the present invention is to provide an apparatus for thermogravimetry in which the weighing of the initial weight of a sample is conducted by the apparatus itself so that the manual work associated with measuring can be minimized.

Particularly, an object of the present invention is to improve the automatic measurement of the initial weight of a sample.

Thermogravimetry apparatus according to the present invention includes a tray on which sample containers are preliminarily disposed, a thermobalance, an automatic conveyance mechanism which conveys the aforesaid sample containers, weight signal processing means including a timer circuit which sets the weighing timing, a processor, and an interface which sends signals from the aforesaid thermobalance to the processor, a first memory which stores the weight of an empty sample container put on a holder, and a second memory which stores the weight of a sample container loaded with a sample, wherein the sample container is put on the holder; and the aforesaid apparatus for thermogravimetry conducts measurements due to the function of the aforesaid processor under the condition that the difference between the content of the aforesaid second memory and that of the aforesaid first memory is the initial weight of the sample. In the aforesaid manner, thermogravimetric analysis for a plurality of samples can be automated.

A necessary number of empty sample containers which have been previously disposed on the tray by a worker, are successively conveyed to the holder by the automatic conveyance mechanism, and weighed by the thermobalance synchronously with a trigger signal sent from the timer circuit. After that, the sample containers are returned to the initial positions on the tray by the automatic conveyance mechanism. At this time, all the weight values of the sample containers are stored in the first memory.

Next, after the worker has put a sample to be measured into each sample container, the automatic conveyance mechanism successively conveys the sample containers loaded with the samples to the holder. Then, the weight value obtained by the thermobalance is stored in the second memory synchronously with a trigger signal sent from the timer circuit. At this time, the processor calculates the difference between the content of the second memory and that of the first memory, and an operation of thermogravimetric analysis is started while the obtained differential value is used as the initial weight.

All the work that the worker must do in a series of measurements is to dispose a necessary number of empty containers on the tray, and to put a sample into each container disposed on the tray. Accordingly, labor on the part of the worker can be greatly reduced. As a result, a plurality of samples are automatically and successive measured by means of thermogravimetry, so that the worker is not occupied with the measurement while a series of measuring operations are carried out.

Therefore, the present invention makes it possible to conduct automatic weighing in the following manner: the weight of an empty sample container is stored in a first memory; the weight of a sample container loaded with a sample is stored in a second memory and the difference of weights stored in the two memories is defined as the initial sample weight.

BRIEF DESCRIPTION OF DRAWING

The sole Figure is a combined perspective view and block diagram showing a preferred embodiment of the present invention.

DESCRIPTION OF THE PREFERRED EMBODIMENTS

With reference to the Figure, an embodiment of the present invention will be described in detail.

In the Figure, numeral 1 is a sample holder made of a platinum-rhodium alloy into which a sample to be analyzed is put. A reference holder 2 is disposed symmetrically with the sample holder 1. The sample holder 1 and the reference holder 2 are respectively connected to section 5 via a sample side balance beam 3 and a reference side balance beam 4. Any weight difference between a sample disposed in the sample holder 1 and that disposed in the reference holder 2 is detected by the balance section 5. As the structure of the balance section 5 is not a novel feature of the present invent detailed explanations are omitted here. The sample holders 1, 2, balance beams 3, 4, section 5, and a heating furnace 6 are defined as a thermobalance section. Heating furnace 6 is moved by a movement mechanism 7. Furnace 6 is horizontally and linearly moved in the direction of the balance beams 3, 4 from a position in which the furnace 6 covers the holders 1, 2, to a position in which the heater 6 does not cover the holders 1, 2. A thermocouple 8 made of platinum-platinum hodium 13% alloy is welded onto the bottom surface of each of the sample holder 1 and the reference holder 2. Components 1 to 7 can concurrently conduct differential thermal analysis and thermogravimetric analysis. Therefore, they form a conventional apparatus for differential thermal analysis.

A plurality of shallow recesses 12a for sample containers 11 are provided in predetermined positions on a tray 12 disposed alongside the thermobalance section so that a plurality of sample containers 11 can be located in the predetermined positions. A sample to be analyzed can be put into each container 11.

Before measurement, a sample container 11 is conveyed to the sample holder 1 by an automatic conveyance mechanism including fingers 13 to pick up the sample container 11, a robot arm 14 carrying fingers 13 at one end, and an arm drive section 15 which moves the sample container 11 picked up by the fingers 13 to a predetermined position by moving the robot arm 14. At this time, in order to stabilize the positions of sample holder 1 and reference holder 2, both the sample side balance beam 3 and the reference side balance beam 4 which hold these holders are supported by a beam clamp 16 so that they can be maintained stationary. The movement of beam clamp 16 is controlled by a clamp drive section 17.

A timer circuit 18 is connected to circuitry in clamp drive section 17, and a period of time from when the clamp drive section 17 has completed its clamp release operation is measured. In addition, timer circuit 18 sends a trigger signal to a processor 22 after a predetermined time period, for example 90 seconds, necessary for stabilizing the balance has passed.

An interface 21 is connected between balance section 5 and processor 22. In the interface 21, a differential thermogravimetric measurement signal, or weight signal, produced in balance section 5 is digitalized and sent to the processor 22. The function of the processor 22 is as follows: it sends weight data, at a point of time when the trigger signal is given, to a first memory 23 or a second memory 24; and when sending the data to the second memory 24, it concurrently subtracts the content of the first memory 23 from the content of the second memory 24 so that the obtained value is outputted as the initial weight data of the sample.

Next, the operation of this embodiment will be explained as follows.

First, prior to measurement, a necessary number of empty sample containers 11 are disposed on the recesses 12a on the tray 12 by a worker. When the worker starts the apparatus in the mode in which the weights of the empty sample containers 11 are measured, first, the heating furnace 6 is moved to uncover holders 1 and 2 by the action of the movement mechanism 7, and the sample holder 1 and the reference holder 2 appear. Next, the clamp drive section 17 is operated, and the sample side balance beam 3 and the reference side balance beam 4, which are extended horizontally, are simultaneously clamped by the beam clamp 16, so that the positions of the sample holder 1 and the reference holder 2 are stabilized. Next, an empty sample container 11 on tray 12 is conveyed to sample holder 1 or reference holder 2 by the automatic conveyance mechanism 13-15. After conveyance of the sample container 11 has been completed, the clamp drive section 17 starts a clamp release operation, and concurrently when the sample side balance beam 3 and the reference side balance beam 4 are released from the beam clamp 16, the timer circuit 18 connected with the clamp drive section 17 starts to measure the time. Further, the heating furnace 6 is moved by the movement mechanism 7 so that the heating furnace covers the sample holder 1 and the reference holder 2 in order to avoid weighing errors caused by an air flow. When a setting time of the timer circuit 18, for example 90 seconds, has passed, the output from the balance section 5 is stored in the first memory 23, via interface 21 and the processor 22, as a weight value.

Next, the heating furnace 6 is moved to uncover holders 1 and 2. After both balance beams 3 and 4 are clamped by the beam clamp 16 again, the sample container 11 is returned to the initial position on the tray 12 by the automatic conveyance mechanism 13-15. Then, the apparatus starts to weigh the next sample container, and in the same manner a series of measurements is completed with regard to a plurality of sample containers 11 taken successively from tray 12.

After a series of measurements has been completed with regard to empty containers, the worker puts a When the measurer starts the apparatus in the mode of sample analysis, the apparatus is driven in the same manner as that described above with respect to empty containers. The explanation of the same procedure is therefore omitted here. When a period of time which was set in the timer circuit 18, for example 90 seconds, has passed, the output from balance section 5 is stored in the second memory 24, via interface 21 and processor 22. At the same time, the difference between the content of the second memory 24 and that of the first memory 23 is calculated by processor 22 as the initial sample weight value. This time, the temperature of the heating furnace 6 is controlled by a conventional temperature control unit (not shown), so that the temperature of a sample is changed, and simultaneous differential thermogravimetric measurement, which includes a further weighing of the sample container with the sample, is started.

After the analysis has been completed, the heating furnace 6 is cooled, then, the sample container 11 is moved to the workers side, and returned to its initial position on the tray 12 by the automatic conveyance mechanism 13-15.

Successively, the next sample container 11 loaded with a sample is conveyed onto the sample holder 1 by the same procedure, and a series of initial weight value measurements and simultaneous differential thermogravimetric measurements are successively repeated. In this manner, differential thermal analysis and thermogravimetric analysis are completed with regard to a series of prepared samples.

In a series of measurements as explained above, the initial weight measurement of a sample, which is essential for differential thermal analysis and thermogravimetric analysis, can be automatically carried out by the apparatus without any effort by a worker.

In the above explanation, a case is explained in which the sample container 3 is put on the sample holder 1 and nothing is put on the reference holder 2. However, it is also possible to operate the apparatus under the condition that a reference sample container is put on the reference holder 2 and a reference sample is put into the reference sample container. In this case, the reference sample container and the reference sample are made of materials which are not changed even when subjected to high temperature. Therefore, the weight change can be neglected in thermogravimetric analysis. Accordingly, measurement can be carried out with one reference sample container and one reference sample. Consequently, it is possible to conduct the aforesaid sample weight measurement under the condition that the reference sample container, or the reference sample container and the reference sample, are put on the reference holder. In the case where the reference sample container and the reference sample are changed for each measurement, the sample weight can be measured in the following manner: the same number of reference sample containers as that of the sample containers 11 are disposed at predetermined positions in recesses 12a on the tray 12; the reference sample container is put on the reference holder 2 by the automatic conveyance mechanism 13, 14, and 15; the empty sample container 11 is put on the sample holder 1; and then the aforesaid operation is carried out. In this case, each time the sample container 11 is changed, the reference sample container is also changed correspondingly.

Timer circuit 18 can be arranged to be capable of providing a plurality of different time periods, one of which is selected for each weighing operation. The selection of a time period can be based, for example, on the expected weight of the container 11 to be weighed. Thus, if the time required for stabilizing a measurement varies as a function of weight, the shortest time period which will assure stabilization can be selected.

As explained above, according to the present invention, thermogravimetric analysis of various kinds of samples can be realized with minimum labor by a worker, and especially the initial weight of a sample can be measured quite automatically. Therefore, errors caused by the worker can be eliminated, so that measurement accuracy can be improved.

This application relates to subject matter disclosed in Japanese Application number 3-213965, filed on Aug. 26, 1991, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An apparatus for performing thermogravimetry measurements comprising: a sample holder for holding a sample container in which a sample can be accommodated; a thermobalance for measuring the weight of a sample container which is held by said sample holder, for producing weight signals representing measured weights and for determining a change of weight of said sample holder, caused by a change of temperature of a sample in the sample container when held in said holder; a tray for holding a plurality of the sample containers in predetermined positions; an automatic conveyance mechanism for conveying a sample container between said tray and said sample holder; a timer circuit for measuring elapsed time according to an operation of said automatic conveyance mechanism, and for generating a trigger signal after a predetermined period of time has elapsed; a processor connected with said timer circuit; an interface connected between said thermobalance and said processor for conducting weight signals from said thermobalance to said processor; a first memory connected with said processor for storing a weight signal output from said thermobalance synchronously with a trigger signal outputted from said timer circuit when an empty sample container is held by said sample holder; and a second memory for storing a weight signal output from said thermobalance synchronously with a trigger signal outputted from said timer circuit when a sample container loaded with a sample to be measured is held by said holder, wherein said apparatus conducts measurement under the condition that the difference between a weight signal stored in said second memory and a weight signal stored in said first memory is the initial weight of a sample to be measured.

2. The apparatus for thermogravimetry according to claim 1, wherein the trigger signal generating time of said timer circuit is adjustable.

3. The apparatus for thermogravimetry according to claim 2, wherein a plurality of different trigger signal generating times can be set in said timer circuit.

4. An apparatus as defined in claim 1 wherein said thermobalance comprises support means for supporting said sample holder, and clamping means for clamping said support means in a fixed position, and wherein said timer circuit is controlled to begin measuring elapsed time in response to operation of said clamping means to unclamp said support means.

5. An apparatus for performing thermogravimetry measurements comprising: a sample holder for holding a sample container in which a sample can be accommodated; a thermobalance for measuring the weight of a sample container which is held by said sample holder, for producing weight signals representing measured weights and for determining a change of weight of said sample holder, caused by a change of temperature of a sample in the sample container when held in said holder; means for holding a plurality of the sample containers in predetermined positions; a conveyance mechanism for conveying a sample container between said holding means and said sample holder; weight signal processing means connected to said thermobalance for receiving each weight signal from the thermobalance; a first memory connected with said processing means for receiving and storing a weight signal output from said thermobalance when an empty sample container is held by said sample holder; and a second memory for storing a weight signal output from said thermobalance when a sample container loaded with a sample to be measured is held by said holder, wherein said apparatus conducts measurements under the condition that the difference between a weight signal stored in said second memory and a weight signal stored in said first memory is the initial weight of a sample to be measured.

6. An apparatus as defined in claim 5 wherein said thermobalance comprises support means for supporting said sample holder, and clamping means movable between a clamping position for clamping said support means in a fixed position and an unclamping position for releasing said support means to permit said thermobalance to measure the weight of a sample container which is held by said sample holder.

* * * * *